United States Patent
Sakai et al.

(10) Patent No.: US 10,239,815 B2
(45) Date of Patent: Mar. 26, 2019

(54) METHOD FOR PRODUCING ACRYLIC ACID

(71) Applicant: NIPPON SHOKUBAI CO., LTD., Osaka (JP)

(72) Inventors: Toyofumi Sakai, Hyogo (JP); Masashi Mukae, Hyogo (JP); Yasutaka Takemoto, Hyogo (JP)

(73) Assignee: NIPPON SHOKUBAI CO., LTD., Osaka (JP)

(*) Notice: Subject to any disclaimer, the term of this patent is extended or adjusted under 35 U.S.C. 154(b) by 0 days.

(21) Appl. No.: 15/548,538

(22) PCT Filed: Jan. 26, 2016

(86) PCT No.: PCT/JP2016/052148
§ 371 (c)(1),
(2) Date: Aug. 3, 2017

(87) PCT Pub. No.: WO2016/125631
PCT Pub. Date: Aug. 11, 2016

(65) Prior Publication Data
US 2018/0022680 A1   Jan. 25, 2018

(30) Foreign Application Priority Data
Feb. 5, 2015   (JP) .................. 2015-021295

(51) Int. Cl.
| B01D 3/26 | (2006.01) |
| B01D 3/32 | (2006.01) |
| B01D 3/40 | (2006.01) |
| C07C 31/20 | (2006.01) |
| C07C 51/44 | (2006.01) |
| C07C 57/04 | (2006.01) |
| C07D 307/60 | (2006.01) |

(52) U.S. Cl.
CPC ............... *C07C 51/44* (2013.01); *B01D 3/26* (2013.01); *B01D 3/40* (2013.01); *C07C 57/04* (2013.01); *B01D 3/322* (2013.01); *B01D 3/324* (2013.01); *C07C 31/202* (2013.01); *C07D 307/60* (2013.01)

(58) Field of Classification Search
CPC ......... C07C 51/42; C07C 51/44; C07C 57/04; C07C 31/202; B01D 3/26; B01D 3/40; B01D 3/322; B01D 3/324; C07D 307/60
See application file for complete search history.

(56) References Cited

U.S. PATENT DOCUMENTS

| 3,888,922 A | 6/1975 | Levy et al. |
| 3,893,895 A | 7/1975 | Dehnert et al. |
| 4,317,926 A | 3/1982 | Sato et al. |
| 4,358,347 A * | 11/1982 | Mettetal ............ B01D 3/34 |
| | | 203/38 |
| 4,365,081 A | 12/1982 | Shimizu et al. |
| 6,180,827 B1 | 1/2001 | Lee et al. |
| 6,352,619 B1 | 3/2002 | Fauconet et al. |
| 6,414,183 B1 | 7/2002 | Saliamoto et al. |
| 6,498,272 B1 | 12/2002 | Schroder et al. |
| 6,679,939 B1 | 1/2004 | Thiel et al. |
| 2009/0149562 A1* | 6/2009 | Nordhoff ............ C07C 51/42 |
| | | 521/149 |
| 2016/0075630 A1 | 3/2016 | Karime et al. |

FOREIGN PATENT DOCUMENTS

| EP | 0 301 879 | 2/1989 |
| EP | 1 749 812 | 2/2007 |
| JP | 60-43055 | 9/1985 |
| JP | 61-35977 | 8/1986 |
| JP | 2000-290225 | 10/2000 |
| JP | 2002-539104 | 11/2002 |
| WO | 2014/189829 | 11/2014 |

OTHER PUBLICATIONS

"Physical Constants of Organic Compounds," in CRC Handbook of Chemistry and Physics, 98th Edition (Internet Version 2018), John R. Rumble, ed., CRC Press/Taylor & Francis, Boca Raton, FL., pp. 3-8, 3-244 and 3-284.*
International Search Report dated Apr. 26, 2016 in International (PCT) Application No. PCT/JP2016/052148.
Office Action dated Nov. 14, 2017 in Japanese Application No. 2016-573294, with English translation.
Extended European Search Report dated May 28, 2018 in European Patent Application No. 16746462.7.

* cited by examiner

*Primary Examiner* — Pancham Bakshi
*Assistant Examiner* — Mark R Luderer
(74) *Attorney, Agent, or Firm* — Wenderoth, Lind & Ponack, L.L.P.

(57) ABSTRACT

The objective of the present invention is to provide a method for efficiently producing acrylic acid while troubles not only in a waste oil handling after distillation of acrylic acid but also in a purification system of acrylic acid during distillation are reduced. The method for producing acrylic acid according to the present invention is characterized in comprising the step of supplying at least crude acrylic acid and an alcohol solvent to an acrylic acid distillation apparatus to distill acrylic acid, wherein a boiling point of the alcohol solvent is higher than a boiling point of acrylic acid by not lower than 50° C.

5 Claims, 2 Drawing Sheets

METHOD FOR PRODUCING ACRYLIC ACID

TECHNICAL FIELD

The present invention relates to a method for efficiently producing acrylic acid with avoiding a trouble in a distillation system of acrylic acid during distillation and a trouble in a handling of waste oil after distillation.

BACKGROUND ART

Acrylic acid is generally produced by subjecting propylene or acrolein to gas-phase catalytic oxidation in the presence of a catalyst to obtain an acrylic acid-containing gas, absorbing the acrylic acid-containing gas with an absorbing liquid or condensing the acrylic acid-containing gas to obtain an acrylic acid aqueous solution, and purifying acrylic acid with distillation or crystallization.

In an acrylic acid production process, a residue obtained by purifying acrylic acid contains a large amount of an impurity but also contains acrylic acid; therefore, acrylic acid is recovered from such a residue by distillation or the like. In addition, the above residue also contains acrylic acid dimer. Acrylic acid dimer is decomposed into acrylic acid to be recovered by heat using a heat decomposition apparatus consisting of a heat decomposition apparatus and an evaporator (Patent Document 1).

A residue after purifying acrylic acid by distillation has high viscosity, since such a residue contains a high-boiling impurity, a polymer and the like. When such a residue after distillation, in other words, a bottom liquid of a distillation apparatus, is discarded, it may be difficult to discharge and transfer the residue from the bottom of the distillation apparatus and the residue may not be stably stored in a storage tank in some cases. Such a problem would further become obvious in a distillation apparatus at latter stage of multistage distillation of acrylic acid and in a step of decomposing acrylic acid dimer by heat.

By the invention described in Patent Document 2, a handling property of waste oil generated from the production process of acrylic acid is improved by adding a solvent selected from water, an alcohol, an ether, a carboxylic acid, a ketone, an aliphatic hydrocarbon or an aromatic hydrocarbon to the waste oil. Patent Document 3 discloses a method for stabilizing a residue liquid remaining on a still after distilling a 2-hydroxyalkyl (meth)acrylate by adding water, acetic acid, salicylic acid, ethanolamines or methanol to the residue liquid.

It is described in Patent Document 4 that a high-boiling residue which remains in a reactor to decompose an acrylic acid oligomer is diluted with an organic acid, such as ethylhexanoic acid and propionic acid, or a hydrophilic organic liquid such as an alkanol, for example, ethanol and methanol in order to be incinerated.

PRIOR ART DOCUMENT

Patent Document

Patent Document 1: JP S61-35977 B
Patent Document 2: JP 2000-290225 A
Patent Document 3: JP S60-43055 B
Patent Document 4: JP 2002-539104 T

DISCLOSURE OF THE INVENTION

Problems to be Solved by the Invention

As described above, a bottom liquid of an acrylic acid distillation apparatus at a disposal stage has a high viscosity, and the invention to improve the handling property of such a bottom liquid by adding a solvent has been developed (Patent Documents 2 and 3). In addition, it is described in Patent Document 4 that a high-boiling residue which remains in a reactor for decomposing an acrylic acid oligomer is diluted to be incinerated.

The more the purification stage goes to the latter, or as the distillation progresses, the viscosity and impurity concentration of the bottom liquid of the distillation apparatus are increased. As a result, waste oil after distillation is difficult to be handled. In addition, a smear adheres on the bottom part of a distillation apparatus during distillation. When acrylic acid dimer is decomposed by heat as described above, a circulation line from a heat decomposition apparatus to an evaporator may become clogged in some cases.

The inventions described in Patent Documents 2 and 3 relate to a handling of waste oil after distillation, and a solvent which is actually added to waste oil is water, acetic acid or methanol in the Examples described in the Patent Documents. If these solvents are added during distillation not after distillation, the above-described troubles during distillation may be reduced but the solvents may be unmixed in acrylic acid obtained from the top of an acrylic acid distillation apparatus. In addition, in the Examples described in Patent Document 4, it is not specifically described that a high-boiling residue is diluted, and a diluent is exemplified by an organic acid or a low-boiling diluent, such as ethanol and methanol.

Under the above-described circumstances, the objective of the present invention is to provide a method for efficiently producing acrylic acid while troubles not only in a waste oil handling after distillation of acrylic acid but also in a purification system of acrylic acid during distillation are reduced.

Means for Solving the Problems

The inventors of the present invention made extensive studies to solve the above problems. As a result, the inventors found that a trouble in a bottom part of a distillation apparatus and waste oil handling system is caused by maleic anhydride mainly. Although the mechanism is not necessarily clear, it is considered that maleic anhydride is decomposed by heat, a radical is generated during the decomposition, and a polymer causing the trouble is produced due to the radical. In addition, maleic acid and maleic anhydride are unavoidably produced in a catalytic gas phase oxidation reaction for producing acrylic acid, and maleic acid is dehydrated by heat to be maleic anhydride. Accordingly, the present inventors completed the present invention by finding that a trouble caused by maleic anhydride in a purification system during distillation and after distillation can be reduced by supplying the specific solvent to an acrylic acid distillation apparatus in addition to crude acrylic acid while the solvent is not unmixed into the acrylic acid obtained from the top of the acrylic acid distillation apparatus.

Hereinafter, the present invention is described.

[1] A method for producing acrylic acid,
comprising the step of supplying at least crude acrylic acid and an alcohol solvent to an acrylic acid distillation apparatus to distill acrylic acid,
wherein a boiling point of the alcohol solvent is higher than a boiling point of acrylic acid by not less than 50° C.

[2] The method according to the above [1], wherein the crude acrylic acid and the alcohol solvent are mixed to obtain a mixture and the mixture is supplied to the acrylic acid distillation apparatus.

[3] The method according to the above [1], wherein the crude acrylic acid and the alcohol solvent are separately supplied to the acrylic acid distillation apparatus.

[4] The method according to any one of the above [1] to [3], wherein a supply amount of the alcohol solvent is adjusted to 1.0 mass % or more to a total amount of maleic acid and maleic anhydride in the crude acrylic acid.

[5] The method according to any one of the above [1] to [4], wherein a polyhydric alcohol is used as the alcohol solvent.

[6] The method according to the above [5], wherein ethylene glycol is used as the alcohol solvent.

Effect of the Invention

In the method for producing acrylic acid according to the present invention, a trouble during distillation, such as an adhesion on the bottom part and a blockage of a circulation line due to a high-viscosity bottom liquid of an acrylic acid distillation apparatus, can be reduced even in a latter distillation stage of a purification step. In addition, even after distillation, a trouble such as a deposition in a pipe for transferring a bottom liquid drawn from an acrylic acid distillation apparatus as waste oil to a storage tank and in a storage tank, and a blockage due to the deposition, can be also reduced; as a result, a bottom liquid drawn from an acrylic acid distillation apparatus can be stably stored as waste oil for a long time. Furthermore, a purity of purified acrylic acid is not substantially decreased in the present invention method. Accordingly, the present invention method is very useful industrially, since acrylic acid can be produced efficiently and stably by the present invention method.

MODE FOR CARRYING OUT THE INVENTION

Figure 1:
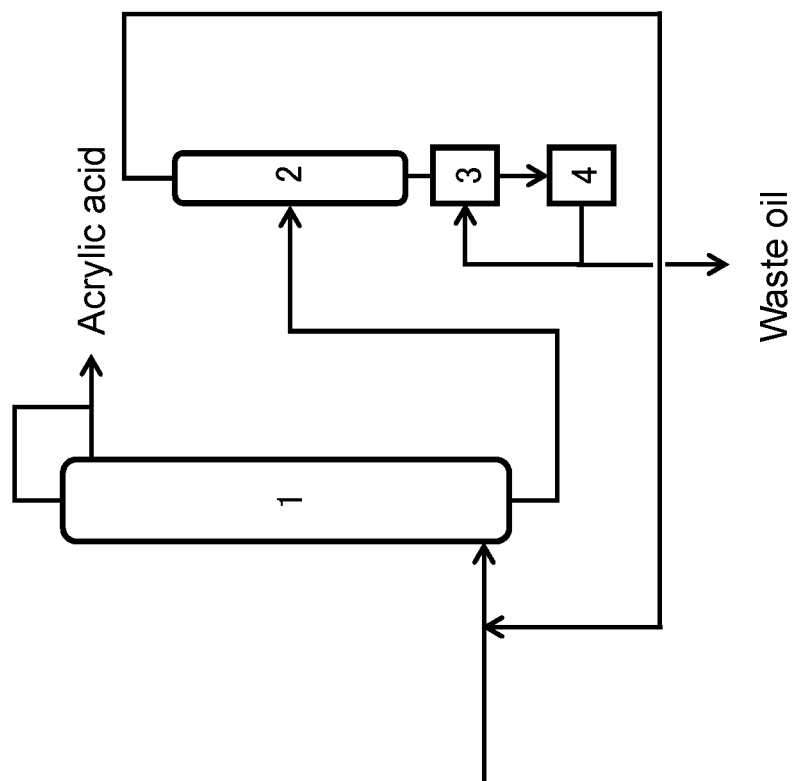
FIG. 1 is a schematic view of an example of a distillation system usable in the present invention method.

The present invention relates to a method for purifying acrylic acid from crude acrylic acid with reducing a trouble in a purification system. Crude acrylic acid can be obtained by a general method. Hereinafter, the present invention is described for each step.

1. Catalytic Gas Phase Oxidation Reaction Step

Acrylic acid can be produced by subjecting a raw material compound such as propylene and acrolein to a catalytic gas phase oxidation reaction. Specifically, for example, a catalyst is packed in a reactor and the reactor is heated to a predetermined temperature range. An oxygen molecule-containing gas, such as oxygen and air, and a raw material gas containing propylene or acrolein are supplied to the heated reactor so that propylene or acrolein is oxidized to obtain an acrylic acid-containing gas.

A composition of a raw material gas may be appropriately adjusted, and for example, a mixed gas consisting of 1 vol % or more and 15 vol % or less of propylene or acrolein, 0.5 vol % or more and 25 vol % or less of molecular oxygen, 0 vol % or more and 30 vol % or less of water vapor, and an inert gas such as nitrogen gas as a remnant can be used.

A catalyst is not particularly restricted as long as the catalyst is used for producing acrylic acid, and for example, a combined metal oxide catalyst containing an oxide of a metal such as molybdenum, vanadium, bismuth and iron is mainly used. In addition, it is possible that propylene as a raw material compound is subjected to an oxidation reaction to obtain acrolein in a former stage and the acrolein is subjected to an oxidation reaction to obtain acrylic acid in a latter stage. In such a case, each catalyst suitable for a reaction of respective stage may be selected and packed in two layers in a reactor. An inert substance layer may be placed between such two-layer catalyst layers.

A reaction condition may be appropriately determined depending on a raw material gas to be used or the like. For example, a reaction temperature may be adjusted to about 200° C. or higher and about 500° C. or lower. When the reaction is performed in two stages as described above, reaction temperatures may be adjusted in each reaction.

2. Absorbing or Condensing Step

Next, the acrylic acid-containing gas obtained in the above-described catalytic gas phase oxidation reaction step is contacted with an absorbing liquid such as water or condensed, so that an acrylic acid aqueous solution is obtained as crude acrylic acid.

Acrylic acid is generally collected by using a collection column. A collection column has an inlet to supply an acrylic acid-containing gas to the lower part and an inlet to supply an absorbing liquid to the upper part. An absorbing liquid supplied to a collection column moves from the upper part to the lower part due to gravity and is counter-currently contacted with an acrylic acid-containing gas supplied to the lower part. On this operation, a water-soluble component in an acrylic acid-containing gas, such as acrylic acid, is dissolved in an absorbing liquid, and the acrylic acid aqueous solution is drawn from the lower part of a collection column. The kind of a collection column is exemplified by a plate column, a packed column, a wetted wall column and a spray column, and such a collection column is designed so that an acrylic acid-containing gas is contacted with an absorbing liquid more efficiently.

Condensation is generally performed by using a condensation column. In a condensation column, an acrylic acid-containing gas supplied to the lower part is cooled to be separated crude acrylic acid and a gas component. By a condensation column, a supplied acrylic acid-containing gas is cooled in a stepwise manner by cooling water, heat exchange or the like so that each component can be separated depending on a boiling point thereof.

Thus obtained crude acrylic acid contains various impurities, and acrylic acid is purified by removing such impurities in the following steps. A purification means may be appropriately selected and a plurality of purification means may be combined depending on the kind of an impurity to be removed or the like.

3. Acrolein Emission Step

The crude acrylic acid obtained by the above-described step 2 contains acrolein as a raw material compound or an intermediate product. It is therefore preferred that the crude acrylic acid is supplied to an acrolein emission column to remove acrolein. The acrolein obtained from the top part of an acrolein emission column may be returned to the above-described catalytic gas phase oxidation reaction step and/or absorbing step or condensing step. The present step may be optionally performed.

4. Removing Water Step

The crude acrylic acid obtained by the above-described step 2 contains water derived from a raw material gas, an absorbing liquid or the like. It is therefore preferred to remove water. The present step may be optionally performed.

In general, an azeotropic separation is performed to remove water from crude acrylic acid. Such an azeotropic separation means that water, acetic acid and the like are removed from crude acrylic acid by distillation with using an azeotropic solvent. A solvent for azeotropy forms an azeotropic mixture with water.

A solvent for azeotropy used in an azeotropic separation is not particularly restricted, and is exemplified by a ketone azeotropic solvent such as diethyl ketone, methyl propyl ketone, methyl isobutyl ketone and methyl t-butyl ketone; an ester azeotropic solvent such as n-propyl acetate; an aromatic hydrocarbon azeotropic solvent such as toluene; an aliphatic hydrocarbon azeotropic solvent such as heptane and methylcyclohexane; and a mixed azeotropic solvent containing the above two or more azeotropic solvents.

An impurity having lower boiling point than acrylic acid may be removed by using a lower-boiling substance separation column before or after an azeotropic separation in order to remove a lower-boiling impurity such as acetic acid.

In general, distillation or crystallization are performed in order to purify acrylic acid from the crude acrylic acid obtained by the above-described steps.

When acrylic acid is purified from crude acrylic acid by crystallization, crude acrylic acid is cooled to produce an acrylic acid crystal and the crystal is separated from a mother liquid. Such a mother liquid contains acrylic acid in addition to an impurity. It is therefore preferred that acrylic acid is recovered from the mother liquid obtained in acrylic acid crystallization step by distillation. In addition, acrylic acid may be directly purified from crude acrylic acid by distillation, and acrylic acid purified by distillation may be further purified by crystallization.

The main objective of the present invention is to reduce a trouble of a purification system due to waste oil separated from acrylic acid by distillation and to improve a handling property of such waste oil. Accordingly, distillation of acrylic acid is hereinafter described.

5. Acrylic Acid Distillation Step

An acrylic acid distillation apparatus used in the acrylic acid distillation step has at least an outlet to draw purified acrylic acid, an inlet to return at least a part of the drawn acrylic acid as an reflux liquid, an inlet to supply a polymerization inhibitor and an inlet to supply crude acrylic acid. An acrylic acid distillation apparatus is exemplified by a plate column having a plurality of shelves inside; a packed column having a packed substance inside; a wetted wall column; and a spray column, and any of these columns can be preferably used. In addition, an acrylic acid distillation apparatus separately having an acrylic acid evaporator may be used. The term "distillation of acrylic acid" in the present invention means to separate by evaporating acrylic acid in crude acrylic acid as a gas by heating crude acrylic acid mainly containing high-boiling impurities as an impurity.

A polymerization inhibitor is not particularly restricted, and is exemplified by a quinone polymerization inhibitor such as hydroquinone and hydroquinone monomethylether (p-methoxyphenol); a phenothiazine polymerization inhibitor such as phenothiazine; a N-oxyl compound polymerization inhibitor such as 2,2,6,6-tetramethylpiperidine 1-oxyl; a copper salt compound polymerization inhibitor such as copper dialkyldithiocarbamate; a manganese salt compound polymerization inhibitor such as manganese dialkyldithiocarbamate; a nitroso compound polymerization inhibitor such as N-nitrosophenylhydroxylamine and a salt thereof. Only one polymerization inhibitor may be used, and two or more polymerization inhibitors may be used in combination.

Acrylic acid may be distilled in one stage or in two or more stages. When acrylic acid may be distilled in one stage, it may be difficult in some cases to achieve both of high purity and high purification efficiency of acrylic acid. Specifically, when it is intended to obtain all of the acrylic acid in crude acrylic acid by distillation in one step, a purity of distilled acrylic acid may be decreased due to an unmixed impurity and a polymerization of acrylic acid may be proceeded due to heat in the bottom of an acrylic acid distillation apparatus despite the presence of a polymerization inhibitor. On the one hand, when acrylic acid is distilled with adjusting an acrylic acid distillate ratio to be relatively low in order to inhibit the contamination of an impurity in distilled acrylic acid and the generation of a polymer, a distillation efficiency is naturally decreased. It becomes possible to achieve both of high purity and high purification efficiency of acrylic acid by a distillation in two or more steps. Specifically, acrylic acid is distilled in a condition of lower distillate ratio in a former stage, and a bottom liquid containing acrylic acid in an acrylic acid distillation apparatus is subjected to further distillation.

The number of the distillation stages is preferably 5 stages or less, more preferably 3 stages or less, and particularly preferably 2 stages.

The above-described distillate ratio of acrylic acid (%) can be calculated by the formula: [(amount of distilled acrylic acid)/(amount of acrylic acid contained in crude acrylic acid supplied to distillation apparatus)]×100.

When acrylic acid is distilled in two or more stages, the viscosity of a bottom liquid in an acrylic acid distillation apparatus becomes higher in a latter stage. Thus, when a general distillation apparatus is used, distillation may become difficult in some cases. In such a case, it is preferred to use an acrylic acid distillation apparatus equipped with a thin film evaporator in order to distill acrylic acid in an efficient way.

When acrylic acid is distilled, an impurity may be increased due to heat in the bottom part of an acrylic acid distillation apparatus. When acrylic acid is distilled in two or more stages, a bottom liquid of an acrylic acid distillation apparatus in a former stage is subjected to distillation of a latter stage. As a result, the above-described impurity may be unmixed into acrylic acid distilled in a latter stage. In such a case, it is preferred that all or a part of distilled acrylic acid obtained in a latter stage is returned to an acrylic acid distillation apparatus in a former stage so that the returned acrylic acid is used as a part of crude acrylic acid in a former stage.

A high-boiling impurity generated as a by-product in an acrylic acid production process is exemplified by acrylic acid dimer, which is generated by Michael addition of acrylic acid. Such acrylic acid dimer is decomposed into acrylic acid again by heat. It is therefore preferred that, in distillation of acrylic acid, a bottom liquid of an acrylic acid distillation apparatus is continuously or intermittently drawn and heated so that acrylic acid dimer is decomposed into acrylic acid, and circulated to the acrylic acid distillation apparatus to recover acrylic acid. When acrylic acid is distilled in two or more stages, a concentration of a high-boiling impurity becomes higher in a latter stage. It is therefore preferred to perform above-described decomposition of acrylic acid dimer in a latter stage of an acrylic acid distillation step.

A temperature for decomposing acrylic acid dimer into acrylic acid by heat may be adjusted to about 120° C. or higher and about 220° C. or lower. A time for heat decomposition of a bottom liquid of an acrylic acid distillation apparatus may be appropriately adjusted, and may be set to, for example, about 1 hour or more and about 100 hours or less. The time for heat decomposition in the case of continuously perform heat decomposition means a residence time of a distillation apparatus bottom liquid in a heat decomposition apparatus and can be adjusted depending on an amount of a bottom liquid drawn from an acrylic acid distillation apparatus and an amount of a bottom liquid returned from a heat decomposition apparatus to an acrylic acid distillation apparatus.

A heat decomposition apparatus for acrylic acid dimer is not particularly restricted as long as acrylic acid can be decomposed into acrylic acid by heat using the apparatus, and is exemplified by a heat decomposition apparatus and a reaction distillation apparatus described in JP 2010-184871 A. A reaction distillation apparatus means an apparatus by which acrylic acid can be distilled with decomposing acrylic acid dimer contained in a bottom liquid of an acrylic acid distillation apparatus by heat.

In the present invention method, at least an alcohol solvent which has higher boiling point than that of acrylic acid by 50° C. or higher is supplied to an acrylic acid distillation apparatus in addition to crude acrylic acid. An acrylic acid polymerization which is considered to be caused by a decomposition of maleic anhydride can be inhibited by supplying such an alcohol solvent. As a result, a trouble, such as an adhesion of a high-boiling impurity on a bottom part and an evaporator of an acrylic acid distillation apparatus, a blockage of a circulation line from a heat decomposition apparatus to an acrylic acid distillation apparatus during a heat decomposition of acrylic acid dimer, a blockage of a pipe for transferring waste oil obtained after distillation, and a generation of deposition in a storage tank of the waste oil, can be reduced. In addition, it may become possible to improve an acrylic acid production efficiency and reduce a total amount of waste oil by sufficiently decomposing acrylic acid dimer into acrylic acid with preventing a polymerization of acrylic acid.

When acrylic acid is distilled in two or more stages, a concentration of a high-boiling impurity in a bottom liquid of an acrylic acid distillation apparatus becomes higher in a latter stage; therefore, an effect by supplying the above-described alcohol solvent to an acrylic acid distillation apparatus can be more effectively exerted in a latter stage of an acrylic acid distillation step. It is preferred that the above-described alcohol solvent is supplied to an acrylic acid distillation apparatus at the last stage of an acrylic acid distillation step, since a bottom liquid of an acrylic acid distillation apparatus after distillation is directly discarded as waste oil.

The alcohol solvent used in the present invention method has a higher boiling point than a boiling point of acrylic acid by 50° C. or higher. Specifically, since the boiling point of acrylic acid is about 141° C. under an ordinary pressure, an alcohol solvent having a boiling point of about 190° C. or higher under an ordinary pressure is used. The term "boiling point" in the present invention means a boiling point under an ordinary pressure.

The alcohol solvent usable in the present invention method is not particularly restricted as long as the alcohol solvent has the above-described boiling point, is a liquid at room temperature (25° C.) under an ordinary pressure and is a hydrocarbon having one or more hydroxy groups as a substituent, and is exemplified by a monovalent alcohol such as n-octanol, n-nonylalcohol, n-decanol, n-undecanol and n-dodecanol; a polyhydric alcohol such as ethylene glycol, propylene glycol and glycerin; a glycol ether such as dipropylene glycol monomethyl ether, diethylene glycol diethyl ether, diethylene glycol monomethyl ether, diethylene glycol butyl methyl ether and tripropylene glycol dimethyl ether. Among the examples, a monovalent alcohol and a polyhydric alcohol are preferred, a polyhydric alcohol is more preferred, ethylene glycol, propylene glycol and glycerin are even more preferred, and ethylene glycol is particularly preferred.

In particular, the above-described alcohol solvent is reacted with maleic anhydride, which is considered to be a cause of a trouble in a distillation system and waste oil handling system, to form a maleic acid ester. It is contemplated that maleic anhydride is decomposed by heat or the like, a radical is generated in the process of the decomposition process, and the radical facilitates a polymerization of acrylic acid. On the one hand, the above-described maleic acid ester does not facilitate a polymerization of acrylic acid, since the maleic acid ester is more difficult to be decomposed than maleic anhydride. In other words, the decomposition of maleic anhydride is presumably inhibited and thus the generation of an acrylic acid polymer is avoided by supplying the above-described alcohol solvent; as a result, the above-described alcohol solvent can effectively prevent a trouble in a purification system and waste oil handling system.

A method for supplying the above-described alcohol solvent to an acrylic acid distillation apparatus is not particularly restricted as long as the alcohol solvent can be mixed with crude acrylic acid in the acrylic acid distillation apparatus. For example, it is possible that crude acrylic acid and the alcohol solvent are mixed to obtain a mixture and the mixture is supplied to an acrylic acid distillation apparatus, or crude acrylic acid and the alcohol solvent are separately supplied to an acrylic acid distillation apparatus which has separate inlets for supplying crude acrylic acid and the alcohol solvent. In addition, it is also possible that a part of the above-described alcohol solvent to be supplied is mixed with crude acrylic acid, the mixture is supplied to an acrylic acid distillation apparatus, and the remaining alcohol solvent is separately supplied through an inlet for supplying the alcohol solvent.

The above-described alcohol solvent or a mixture containing the alcohol solvent may be directly supplied to an acrylic acid distillation apparatus, and alternatively may be supplied in the above absorbing or condensing step, acrolein emission step, water removing step or the like as long as the alcohol solvent is ultimately supplied to an acrylic acid distillation apparatus. In the latter cases, the above-described alcohol solvent is not removed from crude acrylic acid and supplied to an acrylic acid distillation apparatus along with crude acrylic acid, since an impurity having lower boiling point than that of acrylic acid is removed in the acrolein emission step and water removing step.

A supply amount of the above-described alcohol solvent may be appropriately adjusted as long as the effect of the present invention can be exerted, and for example, it is preferred that the amount is adjusted on the basis of a total amount of maleic acid and maleic anhydride. The present inventors searched for a cause of an adhesion on the bottom part of an acrylic acid distillation apparatus, a blockage of a pipe for transferring waste oil, or the like, and found maleic acid and maleic anhydride as the cause. That is, in the present invention, the above-described alcohol solvent is used to reduce the concentration of the impurity in a bottom liquid of an acrylic acid distillation apparatus or a waste oil discarded from the acrylic acid distillation apparatus. As a result, a trouble in acrylic acid purification system such as an adhesion and blockage due to the impurity is suppressed.

Specifically, it is preferred to adjust a supply amount of the above-described alcohol solvent to 1.0 mass % or more and 100 mass % or less to a total amount of maleic acid and maleic anhydride contained in crude acrylic acid supplied to an acrylic acid distillation apparatus. When the ratio is 1.0 mass % or more, the effect of the present invention of reducing a trouble in a purification system can be obtained more surely. On the one hand, when the ratio is too large, a total production efficiency of acrylic acid may be possibly decreased due to excessively increased amount of waste oil. The ratio is therefore preferably 100 mass % or less. The ratio is more preferably 2.0 mass % or more, even more preferably 3.0 mass % or more, even still more preferably 5.0 mass % or more or 8.0 mass % or more, and more preferably 80 mass % or less, even more preferably 40 mass % or less, even still more preferably 20 mass % or less.

In addition, a supply amount of the above-described alcohol solvent may be adjusted to 0.01 mass % or more and 10 mass % or less to a supply amount of crude acrylic acid to an acrylic acid distillation apparatus into which the above-described alcohol solvent is supplied, since it should be simplified to determine a supply amount of the above-described alcohol solvent and acrylic acid itself may be possibly a cause of the above described trouble in an acrylic acid purification system. The ratio is more preferably 0.1 mass % or more, even more preferably 0.2 mass % or more, even still more preferably 0.8 mass % or more, and more preferably 8.0 mass % or less, even more preferably 5.0 mass % or less.

For example, a supply amount of the above-described alcohol solvent may be determined on the basis of a supply amount of crude acrylic acid to an acrylic acid distillation apparatus in which a trouble such as an adhesion should be reduced. Alternatively, the amount may be determined depending on a contained amount of a specific impurity which amount is measured by analyzing a sample of the crude acrylic acid.

According to the method of the present invention, a trouble in an acrylic acid purification system, such as an adhesion of a high-boiling impurity on a bottom part and evaporator of an acrylic acid distillation apparatus during distillation step of acrylic acid, a blockage of a pipe for transferring waste oil obtained by distillation and a generation of deposition in a waste oil tank after distillation, can be reduced.

The present application claims the benefit of the priority date of Japanese patent application No. 2015-21295 filed on Feb. 5, 2015. All of the contents of the Japanese patent application No. 2015-21295 filed on Feb. 5, 2015, are incorporated by reference herein.

EXAMPLES

Hereinafter, the present invention is described in more detail with Examples. The present invention is however not restricted to the following Examples in any way, and it is possible to works the present invention according to the Examples with an additional appropriate change within the range of the above descriptions and the following descriptions. Such a changed embodiment is also included in the technical scope of the present invention.

The following "%" is "mass %" unless otherwise noted.

Example 1

Propylene was subjected to catalytic gas phase oxidation to obtain an acrylic acid-containing gas, and the acrylic acid-containing gas was contacted with water to obtain crude acrylic acid. The crude acrylic acid was supplied to a distillation column "1" of an acrylic acid purification system which is schematically represented as FIG. 1. The acrylic acid obtained by distillation was drawn out of the column top, and a bottom liquid was drawn out of the bottom part at a rate of 800 kg/hr. The amount of acrylic acid contained in the bottom liquid was measured by gas chromatography in the following condition.

Column: DB-WAX, manufactured by Agilent Technologies Japan, Ltd., 30 m×0.53 mm i.d., film thickness: 5 µm
Carrier gas: helium (0.5 kgf/cm$^2$)
Injection temperature: 250° C.
Detector: flame ionization detector
Detection temperature: 250° C.
Column temperature: raising temperature from 50° C. to 220° C. at a rate of 10° C./min In addition, after a part of the above-described bottom liquid was collected as a sample and the collected sample was diluted with water to hydrolyze maleic anhydride in the sample, and a contained amount of maleic acid was measured by liquid chromatography in the following condition. As a result, a total concentration of the maleic acid in the sample and the maleic acid produced by the hydrolysis of the maleic anhydride could be determined. In addition, after a sample was separately collected from the above bottom liquid and the sample was diluted with ethylene glycol to esterize the maleic anhydride in the sample, and the concentration of maleic acid in the sample was measured by liquid chromatography in the following condition. Furthermore, the concentration of the maleic anhydride in the sample was calculated by subtracting the maleic acid concentration in the latter sample from the above-described former total concentration of the maleic acid. The result is shown in Table 1.

Column: Inertsil (registered trademark) ODS-3, manufactured by GL science, 4.6×250 mm, particle size: 5 µm
Eluent: mixed solution of 0.1% phosphoric acid aqueous solution/acetonitrile=6/4 by volume
Flow rate: 1 mL/min
Column temperature: 50° C.
Detector: ultraviolet-visible spectrophotometer
Wavelength for detection: 210 nm

TABLE 1

|  | Bottom liquid | |
| --- | --- | --- |
|  | Composition | Supply rate |
| Acrylic acid | 55.0% | 440.0 kg/hr |
| Maleic acid | 5.3% | 42.4 kg/hr |
| Maleic anhydride | 2.0% | 16.0 kg/hr |

The bottom liquid was supplied to the middle shelf of a distillation column "2" along with 6.5 kg/hr of ethylene glycol. As the distillation column "2", a perforated plate distillation column without weir which was a multistage column having 15 shelves was used. Acrylic acid was distilled under the condition of an operating pressure of 34 mmHg and a reflux ratio of 0.7 while a thin-film evaporator "3" was controlled so that a bottom temperature was adjusted to 89° C. to obtain a liquid containing acrylic acid from the top of the column in a rate of 600 kg/hr. The thin-film evaporator "3" had a heat transfer area of 7.5 m$^2$ and was horizontal.

A can liquid drawn from the thin-film evaporator "3" was supplied to a heat decomposition apparatus "4" having a volume of 11 m³, and acrylic acid dimer was decomposed by heat in the tank at 150° C. with a residence time of 45 hours. A part of the can liquid of the heat decomposition apparatus "4" was returned to the thin-film evaporator "3" with a circulation rate of 2800 kg/hr, and another part of the can liquid was discarded as waste oil at a rate of 200 kg/hr.

The distillate liquid obtained from the distillation column "2" was analyzed; as a result, it was not observed that the supplied ethylene glycol was unmixed into the distillate liquid. In addition, acrylic acid was continuously purified in the above-described condition for 6 months; as a result, the acrylic acid purification system shown as FIG. 1 could be stably operated while a trouble in the acrylic acid purification system due to waste oil, such as an adhesion on from the bottom part of the distillation column "2" through the thin-film evaporator "3" and the heat decomposition apparatus "4", a blockage of the circulation line and the liquid transportation line from the distillation column "2" through the waste oil tank, and a deposition in waste oil in the waste oil tank, did not recognized.

Example 2

Acrylic acid was purified similarly to the above-described Example 1 except that a supply amount of ethylene glycol was changed from 6.5 kg/hr to 2.2 kg/hr. As a result, ethylene glycol was not detected in a distillate liquid. In addition, the acrylic acid purification system could be stably operated without any trouble, such as one exemplified in the above-described Example 1, for 6 months.

Comparative Example 1

Acrylic acid was purified similarly to the above-described Example 1 except that ethylene glycol was not supplied. As a result, an operation had to be stopped after an operation for 2 months, since a pipe for waste oil was clogged.

Comparative Example 2

Acrylic acid was purified similarly to the above-described Example 1 except that 1-heptanol was used in place of ethylene glycol. As a result, 1-heptanol of 1340 ppm was detected in the distillate liquid.

The above-described results are shown in Table 2.

from a crude acrylic acid solution, the operation of the system had to be stopped due to the blockage of the pipe for transferring waste oil. Alternatively, when 1-heptanol as the solvent was supplied, highly pure acrylic acid could not be obtained due to the contamination of the supplied solvent in acrylic acid as the target compound.

On the one hand, when the alcohol solvent having a higher boiling point than a boiling point of acrylic acid by not lower than 50° C. was supplied to waste oil, an acrylic acid could be effectively purified for a long period while a trouble such as a blockage of the pipe for transferring waste oil was not recognized and the supplied solvent was not unmixed into acrylic acid.

Example 3

Figure 2:
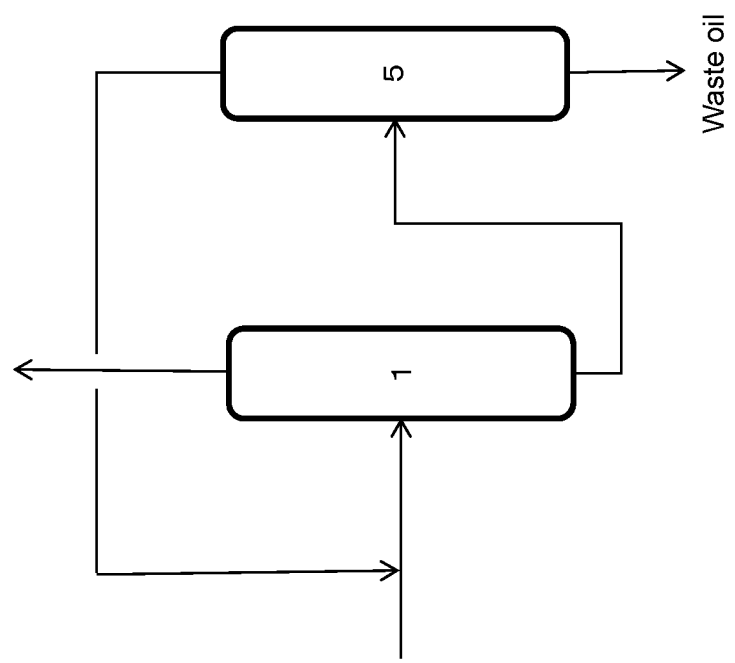
FIG. 2 is a schematic view of an example of a distillation system usable in the present invention method.

A crude acrylic acid solution containing 86.9 mass % of acrylic acid, 5.0 mass % of water, 4.0 mass % of acetic acid, 0.8% of maleic acid, 0.2% of furfural, 0.1% of benzaldehyde and 2.0% of acrylic acid dimer was supplied to the 10th shelf of the distillation column "1" equipped with 20 sieve trays and a reboiler in the acrylic acid purification system schematically shown as FIG. 2 at a rate of 2.54 kg/hr, and acrylic acid was distilled in the condition of a pressure of 93 hPa, a reflux ratio of 0.3 and a bottom temperature of 100° C.

The bottom liquid of the above-described distillation column "1" was supplied at a rate of 190 kg/hr and ethylene glycol was supplied at a rate of 2.1 kg/hr to the 10th shelf of the reaction distillation apparatus "5" equipped with 20 sieve trays and a reboiler.

The bottom liquid of the above-described distillation column "1" was analyzed in a similar condition of the above-described Example 1. The result is shown in Table 3.

TABLE 3

|  | Bottom liquid | |
| --- | --- | --- |
|  | Composition | Supply rate |
| Acrylic acid | 49.7% | 94.4 kg/hr |
| Maleic acid | 9.2% | 17.5 kg/hr |
| Maleic anhydride | 3.8% | 7.2 kg/hr |

In the reaction distillation apparatus "5", acrylic acid was distilled while acrylic acid dimer was decomposed in the

TABLE 2

|  | Added solvent | B.P. of solvent | Supply rate of solvent | Ratio of supplied solvent (vs crude AA) | Ratio of supplied solvent (vs maleic acid + maleic anhydride) | Conc. of solvent in distillate liquid (ppm) | Operation time |
| --- | --- | --- | --- | --- | --- | --- | --- |
| Example 1 | ethylene glycol | 197° C. | 6.5 kg/hr | 0.8% | 11.1% | N.D. | 6 or more months |
| Example 2 | ethylene glycol | 197° C. | 2.2 kg/hr | 0.3% | 3.8% | N.D. | 6 or more months |
| Comparative example 1 | without | — | — | — | — | — | 2 months |
| Comparative example 2 | 1-heptanol | 176° C. | 6.5 kg/hr | 0.8% | 11.1% | 1340 | — |

B.P.: boiling point
AA: acrylic acid
Conc.: concentration

As the result demonstrated in Table 2, when the above solvent was not supplied during a distillation of acrylic acid condition of a pressure of 270 hPa, a reflux ratio of 2, a bottom temperature of 170° C. and a residence time of 10 hours, and the obtained acrylic acid was returned to the above-described distillation column. In addition, the bottom liquid was drawn from the reaction distillation apparatus at a rate of 70 kg/hr, and the drawn bottom liquid was transferred to a waste oil tank as waste oil.

The distillate liquid obtained from the above-described reaction distillation apparatus was analyzed; as a result, the contamination of the added ethylene glycol was not recognized. In addition, acrylic acid was continuously purified in the above-described condition for 2 months; as a result, the acrylic acid purification system could be stably operated while a trouble in the acrylic acid purification system due to waste oil, such as an adhesion on the bottom part of the reaction distillation apparatus, a blockage of a liquid transportation line from the bottom part to the waste oil tank, and a deposition in waste oil in the waste oil tank, did not recognized.

Example 4

Acrylic acid was purified similarly to the above-described Example 3 except that a supplied amount of ethylene glycol was changed from 2.1 kg/hr to 0.7 kg/hr. As a result, the system was stably operated for 2 months while ethylene glycol was not detected in the distillate liquid; however, a little bit of an adhesion on the bottom part and the liquid transportation line of waste oil was observed by a checking after the operation.

Example 5

Acrylic acid was purified similarly to the above-described Example 3 except that a supplied amount of ethylene glycol was changed from 2.1 kg/hr to 4.2 kg/hr. As a result, the system was stably operated for 2 months while ethylene glycol was not detected in the distillate liquid and a trouble in the acrylic acid purification system was not observed.

Example 6

Acrylic acid was purified similarly to the above-described Example 5 except that ethylene glycol was supplied to the column bottom instead of the middle shelf, specifically the 10$^{th}$ shelf in 20 shelves, of the reaction distillation apparatus. As a result, the system was stably operated for 2 months while ethylene glycol was not detected in the distillate liquid and a trouble in the acrylic acid purification system was not observed.

Example 7

Acrylic acid was purified similarly to the above-described Example 3 except that ethylene glycol was changed to glycerin. As a result, the system was stably operated for 2 months while glycerin was not detected in the distillate liquid.

Comparative Example 3

Acrylic acid was purified similarly to the above-described Example 3 except that ethylene glycol was not supplied, the bottom temperature of the reaction distillation apparatus was adjusted to 165° C., and a drawn amount of the bottom liquid was adjusted to 75 kg/hr. As a result, the operation had to be stopped after 2 weeks, since a pipe for transferring waste oil was clogged.

Comparative Example 4

Acrylic acid was purified similarly to the above-described Example 3 except that methanol was supplied instead of ethylene glycol. As a result, methanol was unmixed in the distilled acrylic acid, and the operation had to be stopped after 2 weeks, since a pipe for transferring waste oil was clogged.

Comparative Example 5

Acrylic acid was purified similarly to the above-described Example 3 except that acetic acid was supplied instead of ethylene glycol. As a result, the operation had to be stopped after 2 weeks, since a pipe for transferring waste oil was clogged.

The results of Examples 3 to 7 and Comparative examples 3 to 5 are shown together in Table 4.

TABLE 4

|  | Added solvent | B.P. of solvent | Supply rate of solvent | Ratio of supplied solvent (vs crude AA) | Ratio of supplied solvent (vs maleic acid + maleic anhydride) | Operation time |
|---|---|---|---|---|---|---|
| Example 3 | ethylene glycol | 197° C. | 2.1 kg/hr | 1.1% | 8.5% | 2 or more months |
| Example 4 | ethylene glycol | 197° C. | 0.7 kg/hr | 0.4% | 2.8% | 2 or more months |
| Example 5 | ethylene glycol | 197° C. | 4.2 kg/hr | 2.2% | 17.0% | 2 or more months |
| Example 6 | ethylene glycol | 197° C. | 4.2 kg/hr | 2.2% | 17.0% | 2 or more months |
| Example 7 | glycerin | 290° C. | 2.1 kg/hr | 1.1% | 8.5% | 2 or more months |
| Comparative example 3 | without | — | — | — | — | 2 weeks |
| Comparative example 4 | methanol | 65° C. | 2.1 kg/hr | 1.1% | 8.5% | 2 weeks |
| Comparative example 5 | acetic acid | 118° C. | 2.1 kg/hr | 1.1% | 8.5% | 2 weeks |

B.P.: boiling point
AA: acrylic acid

As the result shown in Table 4, when the solvent was not supplied during the distillation of acrylic acid from a crude acrylic acid solution, the operation of the system had to be stopped due to a blockage of a pipe for transferring waste oil. A similar result was obtained in the case of supplying methanol or acetic acid.

On the one hand, when ethylene glycol or glycerin, which are alcohol solvents having a higher boiling point than that of acrylic acid by not lower than 50° C., was added, acrylic acid could be effectively purified without a serious trouble due to waste oil. But when a ratio of the alcohol solvent to the maleic acid and maleic anhydride contained in crude acrylic acid was less than 3.0 mass %, a little adhesion on the bottom part of the distillation apparatus and the liquid transportation line of waste oil was observed. On the one hand, when the ratio was 3.0 mass % or more, such an adhesion was not observed.

DESCRIPTION OF THE REFERENCE CHARACTERS

1: Distillation column
2: Distillation column
3: Thin-film evaporator
4: Heat decomposition apparatus
5: Reaction distillation apparatus

The invention claimed is:

1. A method for producing acrylic acid,
   comprising the step of supplying at least crude acrylic acid and an alcohol solvent to an acrylic acid distillation apparatus to distill acrylic acid and drawing the acrylic acid out of the top of the acrylic acid distillation apparatus,
   wherein a boiling point of the alcohol solvent is higher than a boiling point of acrylic acid by not lower than 50° C., and
   wherein a supply amount of the alcohol solvent is adjusted to 1.0 mass % or more to a total amount of maleic acid and maleic anhydride in the crude acrylic acid.

2. The method according to claim 1, wherein the crude acrylic acid and the alcohol solvent are mixed to obtain a mixture and the mixture is supplied to the acrylic acid distillation apparatus.

3. The method according to claim 1, wherein the crude acrylic acid and the alcohol solvent are separately supplied to the acrylic acid distillation apparatus.

4. The method according to claim 1, wherein a polyhydric alcohol is used as the alcohol solvent.

5. The method according to claim 4, wherein ethylene glycol is used as the alcohol solvent.

* * * * *